US006342393B1

(12) United States Patent
Hofstadler et al.

(10) Patent No.: US 6,342,393 B1
(45) Date of Patent: Jan. 29, 2002

(54) METHODS AND APPARATUS FOR EXTERNAL ACCUMULATION AND PHOTODISSOCIATION OF IONS PRIOR TO MASS SPECTROMETRIC ANALYSIS

(75) Inventors: Steven Hofstadler, Oceanside; Richard Griffey, Vista, both of CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/235,528

(22) Filed: Jan. 22, 1999

(51) Int. Cl.[7] .................................... G01N 33/00

(52) U.S. Cl. ...................... 436/173; 250/282; 250/288; 250/290; 436/86; 436/89; 436/94

(58) Field of Search .......................... 436/86, 89, 94, 436/173; 250/281–283, 287, 288, 290

(56) References Cited

U.S. PATENT DOCUMENTS 4,581,533 A * 4/1986 Littlejohn et al. .......... 250/282
5,514,788 A 5/1996 Bennett et al. ............ 536/23.1

OTHER PUBLICATIONS

N. Mikami et al, Chemical Physics Letters 1990, 166, 470–474.*
M. V. Gorshkov et al, Anal. Chem. 1997, 69, 1307–1314.*
H. R. Padley et al, Anal. Chem. 1997, 69, 2914–2918.*
M. Welling et al, International Journal of Mass Spectrometry and Ion Processes 1998, 172, 95–114.*
C. S. Creaser et al, Org. Mas Spectrom. 1991, 26, 335–338, Apr. 1991.*
B. M. Chien et al, Int. J. Mass Spectrom. Ion Processes 1994, 131, 149–179.*
J. P. Honovich et al. J. Phys. Chem. 1983, 87, 3755–3758.*
J. N. Louris et al. Int. J. Mass Spectrom. Ion Processes 1987, 75, 345–352.*

(List continued on next page.)

*Primary Examiner*—Arlen Soderquist
(74) *Attorney, Agent, or Firm*—Pennie & Edmonds LLP

(57) ABSTRACT

The present invention discloses novel methods and apparatuses for mass spectrometry. In the methods and apparatuses of the invention, ions are accumulated in an ion reservoir and dissociated with coherent radiation prior to mass analysis. These methods and apparatuses are amenable to mass spectrometric analysis of biomolecules and are particularly usefuil for the sequencing of oligonucleotides, peptides and oligosaccharides.

18 Claims, 5 Drawing Sheets

OTHER PUBLICATIONS

D. F. Hunt et al. Anal. Chim. Acta 1989, 225, 1–10.*

C. B. Lebrilla et al. J. Am. Chem. Soc. 1989, 111, 8593–8598.*

P. H. Hemberger et al. Chem. Phys. Lett. 1992, 191, 405–410, Apr. 1992.*

J. L. Stephenson, Jr. et al. J. Am. Soc. Mass Spectrom. 1994, 5, 886–893.*

M. Toyoda et al. Genshikaku Kenkyu 1996, 41, 67–75.*

J. L. Sephenson, Jr. et al. ACS Symp. Ser. 1996, 619, 512–564.*

R. I. Thompson et al. Proc.—Electrochem. Soc. 1997, 97–14, 70–81.*

A. Ingendoh et al. J. Mass Spectrom. Soc. Jpn. 1997, 45, 247–264.*

D. S. Tonner et al. Anal. Chem. 1997, 69, 4735–4740, Dec. 1997.*

V. H. Vartanian et al. J. Am. Soc. Mass Spectrom. 1998, 9, 1089–1098, Oct. 1998.*

K. Sannes–Lowery et al. Rapid Commun. Mass Spectrom. 1998, 12, 1957–1961.1, Dec. 1998.*

Amster, "Fourier Transform Mass Spectrometry", *J. Mass Spectrom.,* 1996, 31, 1325–1337.

Biemann, K., "Mass Spectrometry of Peptides and Proteins", *Annu. Rev. Biochem.,* 1992, 61, 977–1010.

Bruins et al., "Ion Spray Interface for Combined Liquid Chromatography/Atmospheric Pressure Ionization Mass Spectrometry", *Anal. Chem.,* 1987, 59, 2642–2646.

Cai et al., "Capillary electrohoresis—mass spectrometry", *J. Chromatogr.,* 1995, 703, 667–692.

Cheng et al., "Electrospray Ionization with High Performance Fourier Transform Ion Cyclotron Resonance Mass Spectrometry for the Study of Noncovalent Biomolecular Complexes", in *Techniques in Protein Chemistry,* 1996, vol. 7, 13–21.

Colorado, A. et al., "Use of Infrared Multiphoton Photodissociation with SWIFT for Electrospray Ionization and Laser Desorption Applications in a Quadrupole Ion Trap Mass Spectrometer", *Anal. Chem.,* 1996, 68, 4033–4043.

Cooks, R.G. et al., "Mass Spectrometry: Exact Weights of Atoms, Molecules, and Molecular Fragments", *Acc. Chem. Res.,* 1994, 27(11), 315.

D'Agostino, P.A. et al., "Analysis of Bioactive peptides by liquid chromatography–high–resolution electrospray mass spectrometry", *J. Chrom.,* 1997, 767, 77–85.

Gauthier, J.W. et al., "Sustained Off–resonance irradiation for collision–activated dissociation involving Fourier transform mass spectrometry. Collision–activated dissociation technique that emulates infrared multiphoton dissociation", *Anal. Chim. Acta,* 1991, 246, 211–225.

Hillenkamp et al., "Matrix–Assisted Laser Desorption/Ionizatin Mass Spectrometry of Biopolymers", *Anal. Chem.,* 1991, 63(24), 1193A–1202A.

Hofstadler, S.A. et al., "Isolated Dual Trapped Ion Cell Assembly for Fourier Transform Ion Cyclotron Resonance Mass Spectromety", *Anal. Chem.,* 1991, 63, 2001–2007.

Huang et al., "LC/MS and LC/MS/MS Determination of Protein Tryptic Digests", *J. Am. Soc. Mass Spectrom.,* 1990, 1, 158–165.

Huang et al., "Packed–Capillary Liquid Chromatography/Ion–Spray Tandem Mass Spectrometry Determination of Biomolecules", *Anal. Chem.,* 1991, 63, 732–739.

Ijames, C.F. et al., "Surface–Induced Dissociation by Fourier Transform Mass Spectrometry", *Anal. Chem.,* 1990, 62, 1295–1299.

Little et al., "Infrared Multiphoton Dissociation of Large Multiply Charged Ions for Biomolecule Sequencing", *Anal. Chem.,* 1994, 66, 2809–2815.

Loo, J.A. et al., "Collisional activation and dissociation of large multiply charged proteins produced by electrospray ionization", *Anal. Chim. Acta,* 1990, 241, 167–173.

Marshall et al., "Fouriere Transform Ion Cyclotron Resonance Mass Spectrometry: The Teenage Years", *Anal. Chem.,* 1991, 63(4), A215–A229.

Murray, K.K., "DNA Sequencing by Mass Spectrometry", *J. Mass Spec.,* 1996, 31, 1203–1215.

Price, W.D. et al., "Tandem Mass Spectrometry of Large Biomolecule Ions by Blackbody Infrared Radiative Dissociation", *Anal. Chem.,* 1996, 68, 859–866.

Rockwood, A.L. et al., "Thermally Induced Dissociation of Ions from Electrospray Mass Spectrometry", *Rapid Comm. Mass Spectrom.,* 1991, 5, 582–585.

Senko, M.W. et al., "Collisional Activation of Large Multiply Charged Ions Using Fourier Transform Mass Spectrometry", *Anal. Chem.,* 1994, 66, 2801–2808.

Senko, M.W. et al., "External Accumulation of Ions for Enhanced Electrospray Ionization Fouriere Transform Ion Cyclotron Resonance Mass Spectrometry", *J. Am. Soc. Mass Spectrom.,* 1997, 8, 970–976.

Skoog, D.A. et al., *Principles of Instrumental Analysis, Saunders College,* Second Edition, Philadelphia, PA, 1980, 477–499.

Smith et al., "New Developments in Biochemical Mass Spectrometry: Electrospray Ionization", *Anal. Chem.,* 1990, 62, 882–899.

Vartanian, V.H. et al., "Advances in Trapped Ion Cells for Fourier Transform Ion Cyclotron Resonance Mass Spectrometry", *Mass Spectrom. Rev.,* 1995, 14, 1–19.

Watson, C.H. et al., "Resonance–Enhanced Two–Laser Infrared Multiple Photon Dissociation of Gasesous Ions", *J. Phys. Chem.,* 1991, 95, 6081–6086.

White, F.M. et al., "An External Source 7 T Fourier Transform Ion Cyclotron Resonance Mass Spectrometer with Electrostatic Ion Guide", *Rapid Commun. Mass Spec.,* 1996, 10, 1845–1849.

Williams, E.R. et al., "Efficiency of Collisionally–Activated Dissociation and 193–nm Photodissociation of Peptide Ions in Fourier Transform Mass Spectrometry", *J. Am. Soc. Mass Spectrom.,* 1990, 1, 288–294.

Williams, E.R. et al., "Surface–Induced Dissociation of Peptide Ions in Fourier–Transform Mass Spectrometry", *J. Am. Soc. Mass Spectrom.,* 1990, 1, 413–416.

Winger et al., "High–Resolution Accurate Mass Measurements of Biomolecules Using a New Electrospray Ionization Ion Cyclotron Resonance Mass Spectrometer", *J. Am. Soc. Mass Spectrom.,* 1993, 4(7), 566–577.

Zubarev, R.A. et al., "Electron Capture Dissociation of Multiply Charged Protein Cations. A Nonergodic Process", *J. Am. Chem. Soc.,* 1998, 120, 3265–3266.

M.G. Qian et al., "Procedures for Tandem Mass Spectrometry on an Ion Trap Storage/Reflection Time–of–flight Mass Spectrometer," Rapid Comm. Mass Spectrometry, 1996, vol. 10, pp. 1911–1920.

Jing–Tao Wu et al., "On–line Capillary Separations/Tandem Mass Spectrometry for Protein Digest Analysis by Using an Ion Trap Storage/Relection Time–of–Flight Mass Detector," J. Am. Soc. Mass Spectrom., 1997, vol. 8, pp. 1237–1246.

Ling He et al., "Development of a Capillary High–performance Liquid Chromatography Tandem Mass Spectrometry System Using SWIFT Technology in an Ion Trap/Reflectron Time–of–flight Mass Spetrometer," Rapid Comm. Mass Spectrom., 1997, vol. 11, pp. 1739–1748.

Ce Ma et al., "The design of an atmospheric pressure ionization/time–of–flight mass spectrometer using a beam deflection method," Rev. Sci. Instrum., 1992, vol. 63, pp. 139–148.

S.M. Michael, "An ion trap storage/time–of–flight mass spectrometer," Rev. Sci. Instrum., 1992, vol. 63, pp. 4277–4284.

B.M. Chien et al., "Plasma Source Atmospheric Pressure Ionization Detection of Liquid Injection Using an Ion Trap Storage/Reflectron Time–of–Flight Mass Spectrometer," Anal. Chem. 1993, vol. 65, pp. 1916–1924.

S.M. Michael et al., "Detection of Electrospray Ionization Using a Quadrupole Ion Trap Storage/Reflectron Time–of–Flight Mass Spectrometer," Anal. Chem. 1993, vol. 65, pp. 2614–2620.

* cited by examiner

METHODS AND APPARATUS FOR EXTERNAL ACCUMULATION AND PHOTODISSOCIATION OF IONS PRIOR TO MASS SPECTROMETRIC ANALYSIS

FIELD OF THE INVENTION

The present invention relates to improved methods and apparatus for mass spectrometry. In particular the invention provides methods and apparatus that dissociate ions in an ion reservoir prior to mass spectrometric analysis. The methods and apparatus of the invention can be used in the analysis of ions of peptides, proteins, carbohydrates, oligonucleotides, nucleic acids, and small molecules as prepared by combinatorial or medicinal chemistry.

BACKGROUND OF THE INVENTION

Mass spectrometry (MS) is a powerful analytical tool for the study of molecular structure and interaction between small and large molecules. The current state-of-the-art in MS is such that less than femtomole quantities of material can be readily analyzed using mass spectrometry to afford information about the molecular contents of the sample. An accurate assessment of the molecular weight of the material may be quickly obtained, irrespective of whether the sample's molecular weight is several hundred, or in excess of a hundred thousand, atomic mass units or Daltons (Da). Mass spectrometry can elucidate significant analytical aspects of important biological molecules. One reason for the utility of MS as an analytical tool is the availability of a variety of different MS methods, instruments, and techniques which can provide different pieces of information about the samples.

A mass spectrometer analyzes charged molecular ions and fragment ions from a sample molecule. These ions and fragment ions are then sorted based on their mass to charge ratio (m/z). A mass spectrum is produced from the abundance of these ions and fragment ions that is characteristic of every compound. In the field of biotechnology, mass spectrometry can be used to determine the structure of a biomolecule. Of particular interest is the ability of mass spectrometry to be used in determining the sequence of oligonucleotides, peptides, and oligosaccharides.

Various mass spectrometric techniques can be used to deduce the sequence of an oligonucleotide. Murray, K. K., *J Mass Spec.,* 1996, 31, 1203–1215, which is incorporated herein by reference in its entirety. Two commonly used ionization methods are electrospray ionization (ESI) and matrix-assisted laser desorption/ionization (MALDI). Mass spectrometry is also commonly used for the sequencing of peptides and proteins (see, in general, Biemann, K., *Annu. Rev. Biochem.,* 1992, 61,977–1010, which is incorporated herein by reference in its entirety).

In principle, mass spectrometers consist of at least four parts, (1) an inlet system, (2) an ion source, (3) a mass analyzer and (4) a mass detector/ion-collection system. Skoog, D. A. and West, D. M., Principles of Instrumental Analysis, Saunders College, Philadelphia, Pa., 1980, 477–485. The inlet system permits the sample to be introduced into the ion source. Within the ion source, molecules of the sample are converted into gaseous ions. The most common methods for ionization are electron impact (EI), electrospray ionization, chemical ionization and matrix-assisted laser desorption/ionization (MALDI). A mass analyzer resolves the ions based on mass-to-charge ratios. Analyzers can be based on magnetic means (sector), time-of-flight, quadrupole and Fourier transform mass spectrometry (FTMS). A mass detector collects the ions as they pass through the detector and records the signal. Each ion source can potentially be combined with each type of mass analyzer generating a wide variety of mass spectrometers.

The field of mass spectrometry is rapidly evolving. Improvements in mass spectrometric instrumentation and methodologies are needed to address increasingly challenging applications in a number of research arenas including the physical, biological, and medical sciences. In many implementations ofmass spectrometers based on Penning and Paul traps, ion formation, isolation, and detection take place in the same region of a vacuum chamber and are temporally, rather than spatially, separated. In a typical pulse, sequence ions are alternatively formed and detected; the ionization duty cycle is defined as the fraction of time ions are formed compared to the overall experiment time. Thus, in high resolution measurements, which may take several seconds to perform yet require ionization intervals of only a few milliseconds, the overall ionization duty cycle is only a few percent. A number of approaches have been explored to improve the ionization duty cycle including schemes in which ions are formed and continuously accumulated in an external ion reservoir and periodically gated into the mass analyzer. For example, a Penning trap in the fringing magnetic field of an Fourier transform ion cyclotron resonance (FTICR) mass spectrometer was used to accumulate ions formed by EI during high resolution measurements in the FTICR cell. Hofstadler, S. A. and Laude, D. A, Jr., *Anal. Chem.,* 1991, 63, 2001–2007, which is incorporated herein by reference in its entirety. Senko, M. W. et al. (*J. Amer. Soc. Mass Spectrom.,* 1997, 8, 970–976) demonstrated that an external ion reservoir formed by an rf-only multipole bounded by two electrostatic elements can efficiently accumulate ions generated by electrospray ionization and the ion ensemble can be periodically pulsed into the FTICR cell for mass analysis.

Another means of improving mass spectra is the use of dissociation to fragment the molecular ions. Dissociation strategies for tandem ESI-MS can be separated into two general categories: those which take place in the ESI source prior to mass analysis, and those which take place after the ESI source and often rely on some form of m/z dependent ion manipulation. For example, Loo, J. A. et al. (*Anal. Chim. Acta,* 1990, 241, 167–173) demonstrated that large multiply charged proteins could be effectively dissociated by employing a relatively large voltage difference between the exit of the desolvating capillary and the skimmer cone. Similarly, Rockwood, A. L. et al. (*Rapid Comm. Mass Spectrom.,* 1991, 5, 582–585) demonstrated that ions could be thermally dissociated in the ESI source by heating the desolvation capillary to extreme temperatures. Both of these "in-source" dissociation schemes produce mass spectra which are rich in fragment ions and can provide sequence information for peptides, proteins, or oligonucleotides. Alternatively, a number of post-source dissociation schemes have been presented which are now widely employed. In general, scanning MS/MS instruments such as triple quadrupoles and magnetic sector instruments employ collisionally activated dissociation (CAD) to effect the dissociation of an m/z selected parent ion. Dagostino, P. A., et al., *J Chrom.,* 1997, 767, 77–85. In addition to employing various forms of CAD (Gauthier, J. W., etal., *Chim. Acta,* 1991, 246, 211–225; and Senko, M. W., et al., *Anal. Chem.,* 1994, 66, 2801–2808), FTICR instruments have successfully demonstrated the use of UV-photodissociation (Williams, E. R., et al., *J. Amer. Soc. Mass Spectrom.,* 1990, 1, 288–294), infrared multiphoton dissociation (IRMPD) (Little, D. P., et al., *Anal. Chem.,*

1994, 66, 2809–2815), surface induced dissociation (SID) (Ijames, C. F. and Wilkins, C.L ., *Anal. Chem.,* 1990, 62, 1295–1299; and Williams, E. R., et al., *J Amer. Soc. Mass Spectrom.,* 1990, 1, 413–416), blackbody infrared radiative dissociation (BIRD) (Price, W. D., et al., *Anal. Chem.,* 1996, 68, 859–866), and more recently, electron capture dissociation (ECD) (Zubarev, R. A., et al., *J Am. Chem. Soc.,* 1998, 120, 3265–3266) to fragment precursor ions.

Infrared multi-photon dissociation (IRMPD) uses photodissociation generally in combination with FTICR or quadrupole ion trap mass analyzers. In this method, ions are collected in the FTICR analyzer cell and the laser interacts with ions within the cell. In IRMPD, the laser dissociates ions into fragment ions, as opposed to an ionization method involving lasers, e.g. MALDI. The most common method of ionization used in IRMPD methods is electrospray ionization as this provides more highly charged ions that are more easily dissociated, as compared to MALDI. Little, D. P., et al., *Anal. Chem.,* 1994, 66, 2809–2815. Little, D. P., et al. used IRMPD for protein and nucleotide sequencing. IRMPD has also been used with quadrupole ion trap mass spectrometers. Colorado, A., et al., *Anal. Chem.,* 1996, 68, 4033–4043.

Currently, IRMPD methods are limited to mass spectrometers based on FTICR and QIT. With FTICR methods the kinetic energy release which accompanies the dissociation event can cause a redistribution of the ions in the trapped ion cell. Upon excitation, these ions can obtain a range of cyclotron radii, which precludes high performance mass measurements. Also, the laser irradiation interval is identical for each ion, which limits the dissociation pathways available to the ion.

Although improvements have been made in the mass spectrometric analysis of biomolecules, especially with the use of IRMPD, there remains a need for improved mass spectrometric methods and apparatuses.

BRIEF DESCRIPTION OF THE DRAWINGS

FIG. 2 is a series of mass spectra for a 20-mer oligonucleotide.

SUMMARY OF THE INVENTION

Figure 1:
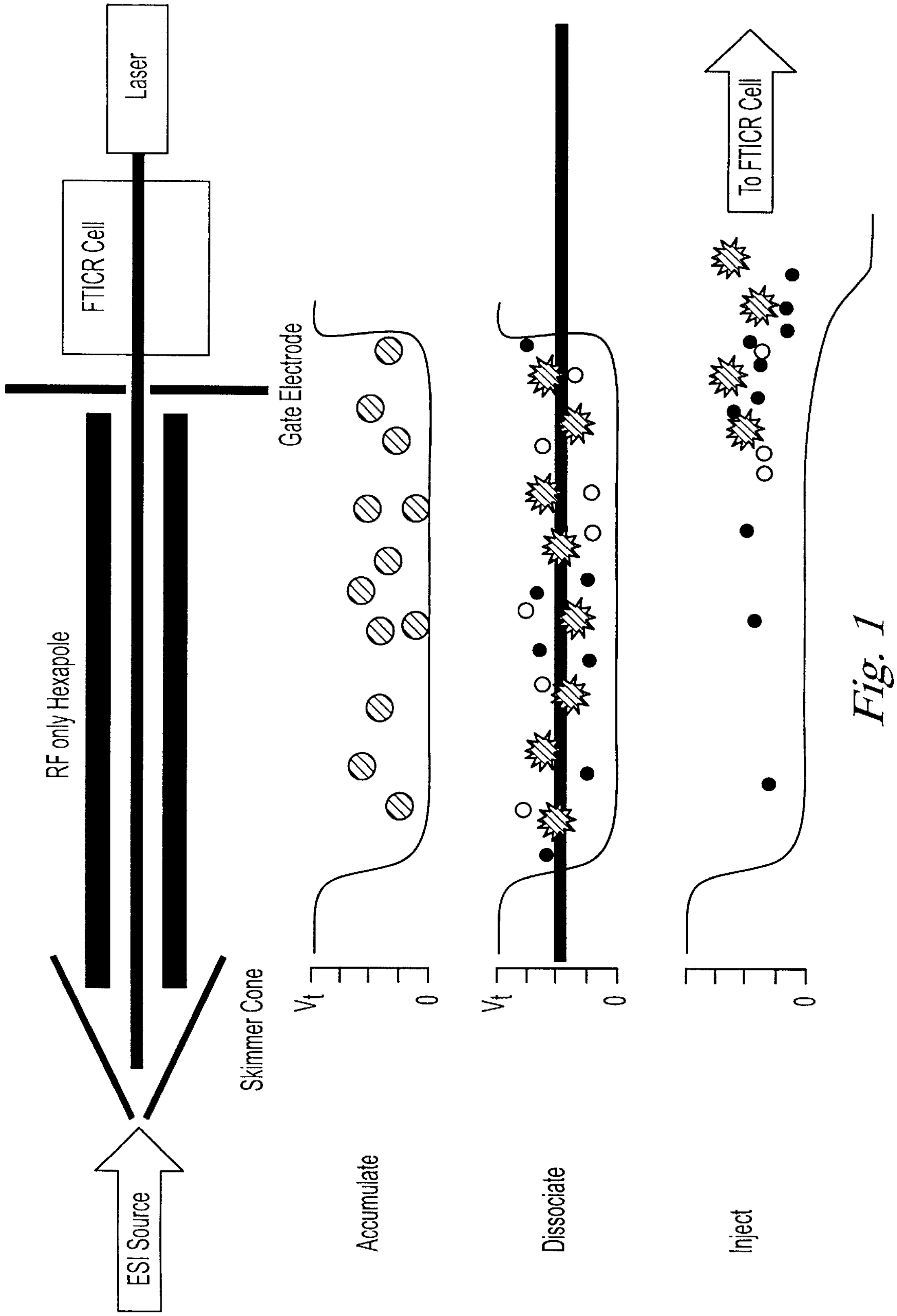
FIG. 1 is a schematic representation of one embodiment of amass spectrometer using external ion reservoir accumulation of ions. Also shown is a representation of the electrostatic potentials used.

The present invention describes methods and apparatuses for inducing controlled dissociation ofmolecular ions external to a mass analyzer of a mass spectrometer prior to mass measurement. The methods and apparatuses comprise generating said ions, collecting said ions in an ion reservoir, and dissociating said ions by application of coherent radiation prior to analysis in a mass analyzer of a mass spectrometer. In preferred embodiments, the ion reservoir is a rf multi-pole ion reservoir and the coherent radiation is applied by a laser. The apparatuses of the invention may be self-contained units that are capable of being retrofitted to many types of mass spectrometers or may be complete mass spectrometers in themselves.

The present invention provides methods and apparatuses that dissociate ions external to a mass analyzer of a mass spectrometer prior to mass spectrometric analysis. These methods and apparatuses can be used for the analysis of singly or multiply charged ions of peptides, proteins, carbohydrates, oligonucleotides, nucleic acids, and small molecules as prepared by combinatorial or medicinal chemistry. The present invention is especially useful for the sequence analysis of peptides and proteins, synthetic oligonucleotides, chemically modified oligonucleotides, RNA, DNA, and oligosaccharides. For modified oligonucleotides that are refractory to conventional enzymatic degradation, the methods of the invention provide a rapid means of sequence analysis. In addition, the identity of small molecules and their presence in tissue extracts, for example, may be determined by this method.

The methods and apparatuses of the invention provide enhanced sensitivity and unexpected ion abundances compared to dissociation of ion in the mass analyzer, as exemplified by IRMPD using Fourier transform ion cyclotron (FTICR) or quadrupole ion trap (QIT). This is due to enhanced ion statistics during the accumulation process in the external ion reservoir. Additional advantages include an improved duty cycle and enhanced ease of operation.

In the present invention, ions of interest are first generated using conventional ionization techniques. These ions are collected in an ion reservoir, where dissociation of the ions occurs. Mass analysis of the dissociated ions is then performed. The ion reservoir is preferably driven at a frequency that captures the ions of interest. These collected ions are dissociated by application of coherent radiation from, for example, an infrared laser. In a preferred embodiment, the gas pressure around the ion reservoir is reduced to $10^{-3}$–$10^{-6}$ torr by vacuum pumping. Following dissociation, the ensemble of ions is transported into the mass analyzer such as by removing or reversing the electric field generated by gate electrodes on either side of the ion reservoir.

Ionization of molecules results in charged particles that can be manipulated by electrostatic potentials. Many ionization methods used with mass spectrometry are amenable to the invention. These include electrospray, chemical, MALDI, laser desorption ionization (LDI), fast atom bombardment (FAB), electron ionization, thermospray ionization, secondary ion mass spectrometry (SIMS), liquid SIMS, field desorption (FD), and $^{252}$Cf desorption (see Constantin, E. and Schnell, A., *Mass Spectrometry,* Ellis Horwood, New York, 1990). Other types of ionization methods are also amenable to the present invention.

The ion reservoir may be a quadrupole, hexapole, octapole or other rf-multi-pole ion reservoir (rf is a shorthand notation for radio frequency). In a rf-multi-pole, a field is formed by pairs of parallel, electrically conducting rods. Each pair of electrodes is electrically connected. A rf oscillator supplies a positive signal to one electrode in each pair and a signal of opposite charge and equal strength to the other electrode in each pair. Another ion trap based on radio frequency is a Paul trap. Cooks, R. G., et al., *Acc. Chem. Res.,* 1994, 27, 315. Other possible ion reservoirs include Penning traps (Vartanian, V. H., et al., *Mass Spectrometry Reviews,* 1995, 14, 1–19), electrostatic lenses, jet expansion and electrostatic ion reservoirs (White, F. M., et al., *Rapid Comm. in Mass Spec.,* 1996, 10, 1845–1849). The ion reservoir may be used to collect negatively or positively charged ions generated by the ion source. The ion reservoir preferably has a gated electrode to allow the accumulation of ion fragments prior to their mass measurement.

Ions are preferably collected in the ion reservoir in a generally mass-inselective manner. This permits dissociation over a broad mass range, with efficient retention of fragment ions. By "mass-inselective", it means that ions are not collected based on their mass to charge ratio. Theoretically, all ions are collected regardless of their mass. From a practical standpoint, those skilled in the art will recognize that there are lower and upper limits to the size of ions that are collected. With the limitation of current instruments, this m/z range is from about 50 to about 100,000 m/z. The ion reservoir also provides a spatial separation which results in a more time-efficient method of mass spectrometry. Thus, the dissociation and measurement take place concurrently in spatially distinct regions of the spectrometer. Mass measurement requires lengthy times. Thus, an improved ionization duty cycle results, which enables improved analysis of on-line separations, e.g. capillary electrophoresis (CE), or liquid chromatography (LC). With the methods of the present invention, an accumulation/dissociation efficiency of near unity can be achieved.

In preferred embodiments of the present invention, dissociation occurs in a relatively high pressure ($10^{-3}$–$10^{-6}$ torr). This results in two advantages over traditional IRMPD as exemplified in FTICR and QIT mass spectrometry. Under high pressures, collisions with neutrals damp the ion cloud to the center of the well and stabilize fragment ions, resulting in significantly improved fragment ion retention. In addition, the fragment ion coverage is significantly improved, giving more sequence information.

The expanded range of fragment ions observed may be the result of at least two contributing factors. First, performing IRMPD during the external ion accumulation event means that ions accumulated in the external ion reservoir can experience a range of irradiation intervals if the laser is activated concurrent with ion injection. For example, in a 500 ms accumulation/dissociation interval, an ion trapped within the first 10 ms of the event will have the opportunity to be irradiated for nearly 500 ms while an ion trapped near the end of the event may be exposed to the laser beam for only a few milliseconds. Additionally, performing the dissociation in the high pressure region ofthe ion reservoir allows collisional focusing, and potentially collisional stabilization of metastable fragments, and mitigates the potential for a spatially defocused ion cloud in the trapped ion cell.

The coherent radiation used in the invention interacts with the molecular ions to dissociate them into fragments. Any coherent radiation source can be used with the invention provided the molecular ions absorb photons at the wavelength emitted by the coherent radiation source. The preferred coherent radiation of the invention is emitted by a laser. Infrared lasers, operating from 1 to about 12 mm, both continuous wave (CW) and pulsed, are amenable to the invention. Ultraviolet lasers, operating from about 150 to 400 nm, generally pulsed, are also amenable to the invention. In a preferred embodiment the laser operates at a wavelength in the infrared region. Typical lasers that may be used in the invention include $CO_2$ lasers, CO lasers and Nd-YAG lasers.

In one embodiment, the coherent radiation emitted from the laser is parallel to the rf-poles and its beam is centered within the rf-multi-pole, i.e, is coaxial relative to the ion reservoir. In another embodiment, the coherent radiation emitted by the laser interacts with the ion volume in an orientation other than a coaxial orientation, e.g. at an oblique angle. The laser may be placed at an angle that permits multiple passes through the ion cloud with the walls of the ion reservoir, e.g. a White cell (Watson, C. H., et al., *J Phys. Chem.,* 1991, 95, 6081–6086), or a single pass perpendicular to the flight path ofthe ions. When multiple passes through the ion cloud are desired, the walls of the ion reservoir have reflective surfaces. It is known by those skilled in the art to provide optics in the ion reservoir to permit the coherent radiation to interact with the fragmented ions.

Ions are accumulated in the ion reservoir external to the mass analyzer of a mass spectrometer. A preferred gated electrode prevents ions from entering the mass analyzer until desired. Once a sufficient ion population is accumulated in the ion reservoir, the voltage potential can be shifted or removed to allow the ions to enter the mass analyzer.

The present invention modifies traditional IRMPD methods in mass spectrometers based on FTICR and QIT. It also permits the use of IRMPD methods in mass spectrometers based on detection schemes other than FTICR and QIT. Many other types of mass analyzers are also amenable to the invention. The invention is equally applicable to Fourier transform ion cyclotron, quadrupole ion trap (i.e. Paul trap), time-of-flight, electric/magnetic sector, quadrupole, and hybrid mass spectrometers. In preferred embodiments, the mass analyzer is composed of a Fourier transform ion cyclotron mass spectrometer, a time-of-flight mass spectrometer, or a quadrupole ion trap (i.e. Paul trap) mass spectrometer.

In an embodiment ofthe invention, an apparatus for ion dissociation comprises an ion reservoir that is capable of receiving and accumulating ions from an ion source and transporting ions or dissociated ions to a mass analyzer, and a coherent radiation source capable of emitting coherent radiation for dissociating ions within the ion reservoir prior to mass analysis. It is envisioned that this apparatus will be self-contained and capable of being retrofitted to present generation mass spectrometers. Thus, a mass spectrometer can be adapted to transfer dissociated ions to a mass analyzer e.g. by providing a conduit from the ion reservoir to the mass analyzer. No additional elaborate optics are required. This provides a cost-effective means of implementing IRMPD.

Alternatively, a mass spectrometer may comprise the apparatus for dissociation in combination with an ion source and a mass analyzer.

Mass spectrometry ion sources are well known in the art. One such ion source uses electrospray ionization mass spectrometry (ESI–MS). Smith et al.,*Anal. Chem.,* 1990, 62, 882–899; Snyder, in Biochemical and biotechnological applications of electrospray ionization mass, American Chemical Society, Washington, D.C., 1996; and Cole, in Electrospray ionization mass spectrometry: fundamentals, instrumentation, Wiley, N.Y. 1997. ESI produces highly charged droplets of the sample being studied by gently nebulizing the sample solution in the presence of a very strong electrostatic field. This results in the generation of highly charged droplets that shrink due to evaporation of the neutral solvent and ultimately lead to a "Coulombic explosion" that affords multiply charged ions of the sample material, typically via proton addition or abstraction, under mild conditions. ESI-MS is particularly useful for very high molecular weight biopolymers such as proteins and nucleic acids greater than 10 kDa in mass, for it affords a distribution of multiply-charged molecules of the sample biopolymer without causing any significant amount of fragmentation. The fact that several peaks are observed from one sample, due to the formation of ions with different charges, contributes to the accuracy of ESI-MS when determining the molecular weight of the biopolymer because each observed peak provides an independent means for calculation of the molecular weight of the sample. Averaging the multiple readings of molecular weight so obtained from a single ESI-mass spectrum affords an estimate of molecular weight that is much more precise than would be obtained if a single molecular ion peak were to be provided by the mass spectrometer. Further adding to the flexibility of ESI-MS is the capability to obtain measurements in either the positive or negative ionization modes.

Matrix-Assisted Laser Desorption/Ionization Mass Spectrometry (MALDI-MS) is another ion source method that can be used for studying biomolecules. Hillenkamp et al., Anal. Chem., 1991, 63, 1193A–1203A. This technique ionizes high molecular weight biopolymers with minimal concomitant fragmentation ofthe sample material. This is typically accomplished via the incorporation of the sample to be analyzed into a matrix that absorbs radiation from an incident UV or IR laser. This energy is then transferred from the matrix to the sample resulting in desorption ofthe sample into the gas phase with subsequent ionization and minimal fragmentation. One of the advantages of MALDI-MS over ESI-MS is the simplicity of the spectra obtained as MALDI spectra are generally dominated by singly charged species. Typically, the detection of the gaseous ions generated by MALDI techniques, are detected and analyzed by determining the time-of-flight (TOF) of these ions. While MALDI-TOF MS is not a high resolution technique, resolution can be improved by making modifications to such systems, by the use of tandem MS techniques, or by the use of other types of analyzers, such as Fourier transform (FT) and quadrupole ion traps.

Fourier transform mass spectrometry (FTMS) is mass detection technique and is especially useful because of its ability to make mass measurements with a combination of mass measurement accuracy and resolution that is superior to other MS detection techniques, in connection with ESI or MALDI ionization. Amster, J. Mass Spectrom., 1996, 31, 1325–1337. Further it may be used to obtain high resolution mass spectra of ions generated by any of the other ionization techniques. The basis for FTMS is ion cyclotron motion, which is the result of the interaction of an ion with a unidirectional magnetic field. The mass-to-charge ratio of an ion (m/q or m/z) is determined by a FTMS instrument by measuring the cyclotron frequency of the ion. The insensitivity of the cyclotron frequency to the kinetic energy of an ion is one of the fundamental reasons for the very high resolution achievable with FTMS. FTMS is an excellent detector in conventional or tandem mass spectrometry, for the analysis of ions generated by a variety of different ionization methods including ESI and MALDI, or product ions resulting from collisionally activated dissociation (CAD).

Collisionally activated dissociation (CAD), also known as collision induced dissociation (CID), is a method by which analyte ions are dissociated by energetic collisions with neutral or charged species, resulting in fragment ions which can be subsequently mass analyzed. Mass analysis of fragment ions from a selected parent ion can provide certain sequence or other structural information relating to the parent ion. Such methods are generally referred to as tandem mass spectrometry (MS or MS/MS) methods and are the basis of the some of MS based biomolecular sequencing schemes being employed today.

FTICR-MS, like ion trap and quadrupole mass analyzers, allows selection of an ion that may actually be a weak non-covalent complex of a large biomolecule with another molecule (Marshall and Grosshans, Anal. Chem., 1991, 63, A215-A229; Beu et al., J. Am. Soc. Mass Spectrom., 1993, 4, 566-577; and Winger et al., J. Am. Soc. Mass Spectrom., 1993, 4, 566-577); (Huang and Henion, Anal. Chem., 1991, 63, 732-739), and is compatible with hyphenated techniques such as LC-MS (Bruins, Covey and Henion, Anal. Chem., 1987, 59, 2642–2646; Huang and Henion, J. Am. Soc. Mass Spectrom., 1990, 1, 158–65; and Huang and Henion, Anal. Chem., 1991, 63, 732–739) and CE-MS (Cai and Henion, J. Chromatogr., 1995, 703, 667–692) experiments. FTICR-MS has also been applied to the study of ion-molecule reaction pathways and kinetics.

Typically, tandem mass spectrometry ($MS^n$) involves the coupled use of two or more stages of mass analysis where both the separation and detection steps are based on mass spectrometry. The first stage is used to select an ion or component of a sample from which further structural information is to be obtained. This selected ion is then fragmented by (CID) or photodissociation. The second stage of mass analysis is then used to detect and measure the mass of the resulting fragments or product ions. The advent of FTICR-MS has made a significant impact on the utility of tandem, $MS^n$ procedures because of the ability of FTICR to select and trap specific ions of interest and its high resolution and sensitivity when detecting fragment ions. Such ion selection followed by fragmentation routines can be performed multiple times so as to essentially completely dissect the molecular structure of a sample. A two-stage tandem MS experiment would be called a MS-MS experiment while an n-stage tandem MS experiment would be referred to as a $MS^n$ experiment. Depending on the complexity of the sample and the level of structural detail desired, $MS^n$ experiments at values of n greater than 2 may be performed.

Ion trap-based mass spectrometers are particularly well suited for such tandem experiments because the dissociation and measurement steps are temporally rather than spatially separated. For example, a common platform on which tandem mass spectrometry is performed is a triple quadrupole mass spectrometer. The first and third quadrupoles serve as mass filters while the second quadrupole serves as a collision cell for CAD. In a trap based mass spectrometer, parent ion selection and dissociation take place in the same part of the vacuum chamber and are effected by control of the radio frequency wavelengths applied to the trapping elements and the collision gas pressure. Hence, while a triple quadrupole mass analyzer is limited to two stages of mass spectrometry (i.e. MS/MS), ion trap-based mass spectrometers can perform $MS^n$ analysis in which the parent ion is isolated, dissociated, mass analyzed and a fragment ion of interest is isolated, further dissociated, and mass analyzed and so on. A number of $MS^4$ procedures and higher have appeared in the literature in recent years. Cheng et al., Techniques in Protein Chemistry VII, Academic Press, Inc., 1996, 7, 13–21.

EXAMPLES

Example 1

Instrumentation

All experiments were performed on a Bruker DALTONICS (Billerica, Mass.) Apex 70e Fourier transform ion cyclotron resonance mass spectrometer. The spectrometer is equipped with an Analytica (Branford, Conn.) electrospray source utilizing a grounded ESI emitter, a counter current drying gas, a glass desolvation capillary, a single skimmer cone, and an rf-only hexapole ion reservoir. Ions are accumulated in the external ion reservoir for 500 ms and pulsed into the INFINITY™ trapped ion cell where they are analyzed by FTICR. All aspects of the experiment including data acquisition, processing, and plotting were performed using Bruker XMASS version 4.0 running on a Silicon Graphics R5000 workstation. A 17 mM solution of Isis 2302, a 20-mer phosphorothioate oligonucleotide (synthesized as described in U.S. Pat. No. 5,514,788, herein incorporated by reference) was electrosprayed from a 50:50 isopropanol:water solution containing 0.1% tripropyl amine through an off-axis electrospray probe at a flow rate of 1.5 mL/minute.

IRMPD. As shown in FIG. 1, the external ion accumulation region is comprised of a biased skimmer cone, an rf-only hexapole operating at 5 MHz (500 Vpp), and an auxiliary "gate" electrode at the low pressure end of the hexapole. The capillary exit voltage is maintained at −68 V to avoid fragmentation due to conventional nozzle-skimmer dissociation, or −180 V to induce nozzle-skimmer dissociation. For operation in the negative ionization mode, the potential of the skimmer cone is typically held at −15 V while the gate electrode toggles between −15 V during accumulation and 0.2 V during injection; the polarity of these electrodes is reversed for operation in the positive ionization mode. IRMPD of ions in the external ion reservoir was effected by irradiation at 10.6 mm from a Synrad (Mukitelo, Wash.) 25 W CW $CO_2$ laser. A lab-built aluminum optical bench was positioned approximately 1.5 m from the actively shielded superconducting magnet such that the laser beam was aligned with the central axis of the magnet. Using standard IR compatible mirrors and kinematic mirror mounts, the unfocused 3 mm laser beam was aligned to traverse directly through the 3.5 mm holes in the trapping electrodes of the INFINITY™ trapped ion cell and longitudinally traverse the hexapole region of the external ion reservoir finally impinging on the skimmer cone. Alignment was accomplished by a preliminary visual alignment with a visible diode laser such that light could be seen exiting the glass desolvation capillary at the source-end of the spectrometer. Subsequent alignment was optimized by the mass spectral fragmentation response with the IR laser triggered during the ion accumulation interval. The laser was operated at an output of 28 watts as measured at the entrance to the mass spectrometer.

Example 2

Comparison of Mass Spectrometry Methods With an Oligonucleotide

ESI-FTICR spectra of a 20-mer phosphorothioate oligonucleotide were acquired from a 17 mM 50:50 $H_2O$:isopropanol solution with 0.1% tripropylamine. Each spectrum was acquired following a 500 ms ion accumulation interval in the external ion reservoir, a) employing a standard detection sequence, b) employing an in-cell IRMPD pulse sequence which incorporates a 100 ms laser pulse from a CO2 laser (10.6 mm), c) identical conditions as in a) except the laser is traversing the external ion reservoir during the 500 ms ion accumulation interval effecting IRMPD in the external ion reservoir.

Figures 2A, 2B:
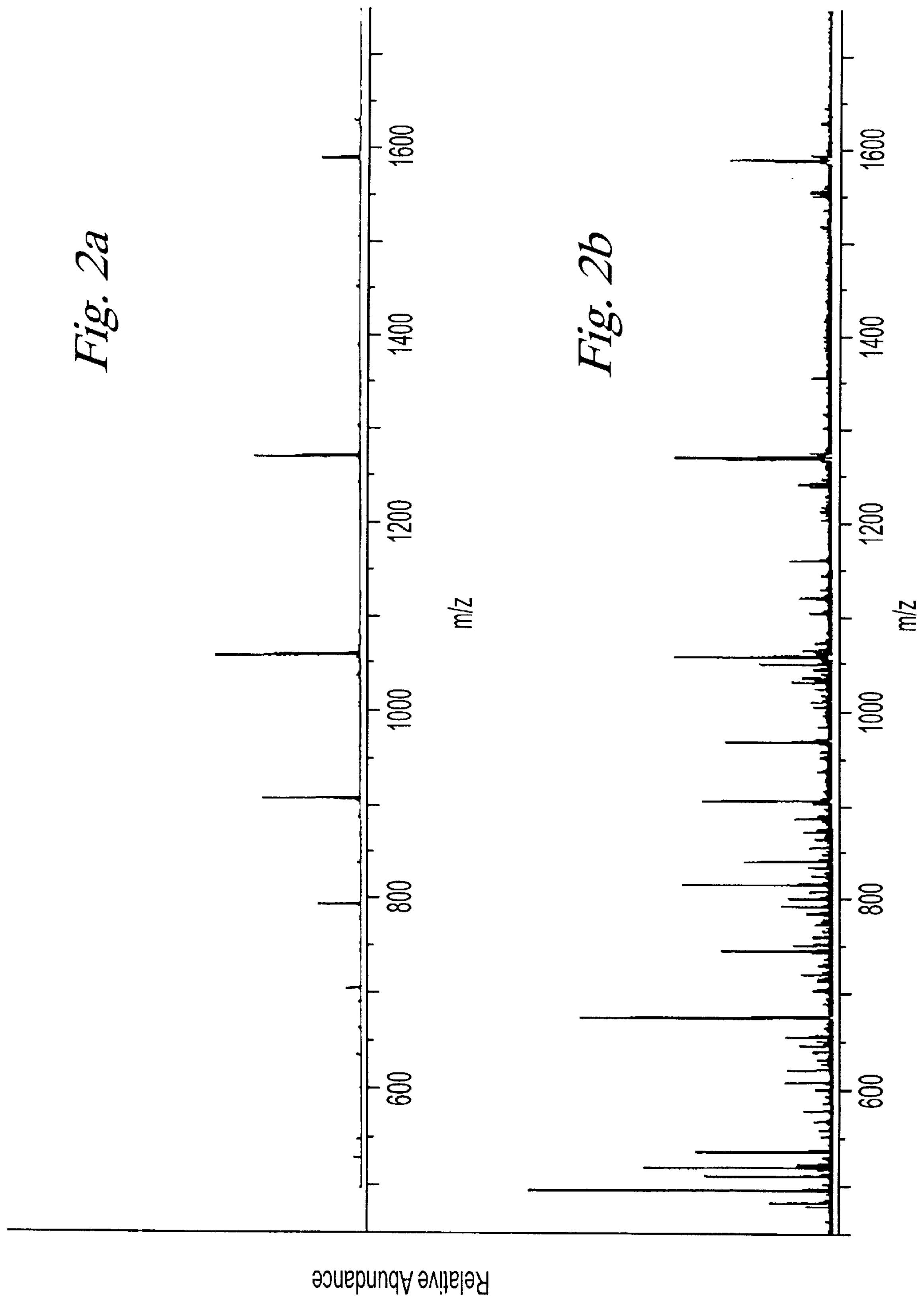
FIG. 2*a* represents non-IRMPD mass spectrometry.
FIG. 2*b* represents traditional in-cell IRMPD.
Figure 2C:
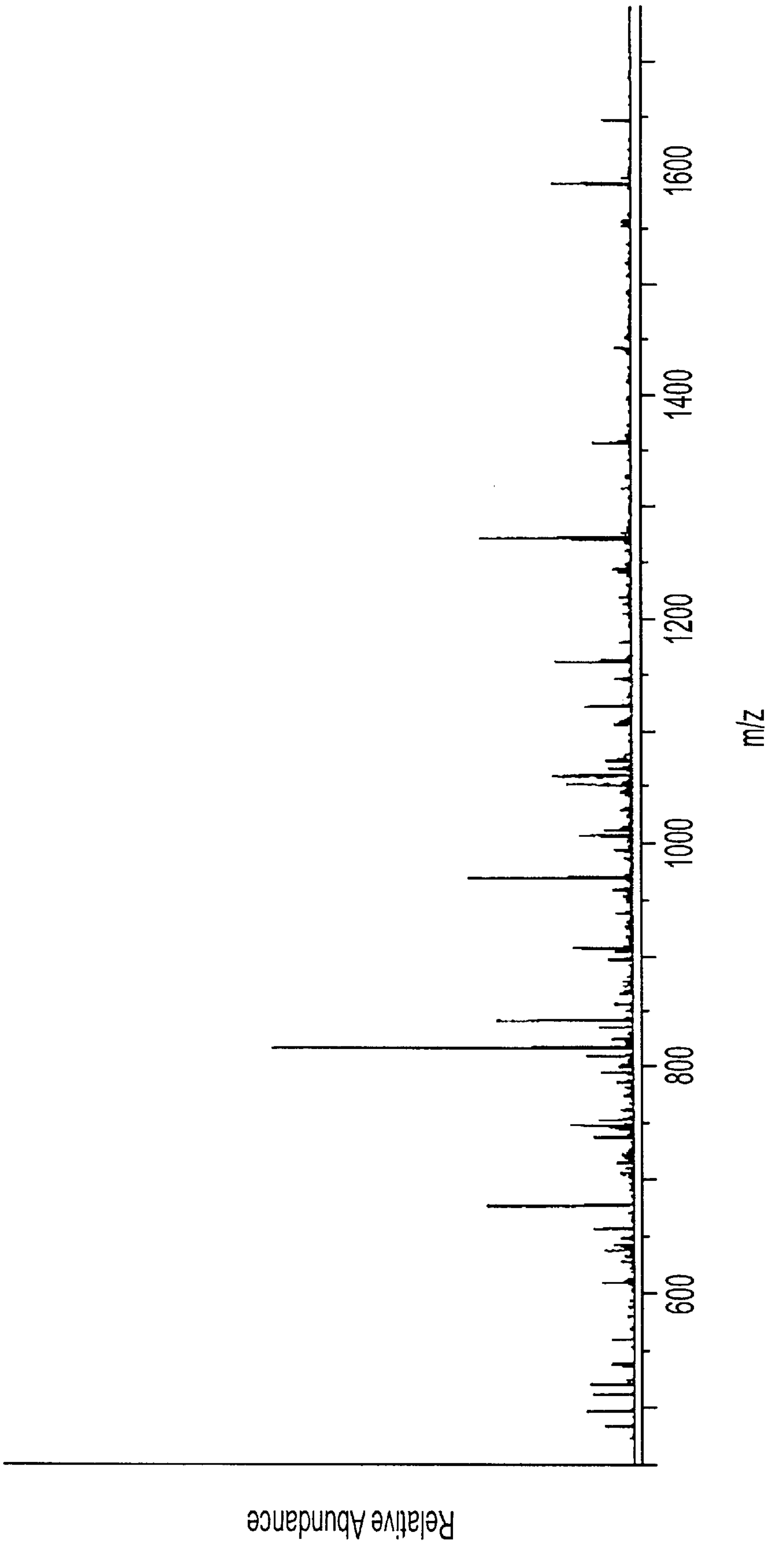
FIG. 2*c* represents IRMPD in which the dissociation was performed in the external ion reservoir concurrent with ion accumulation.
Figure 3A:
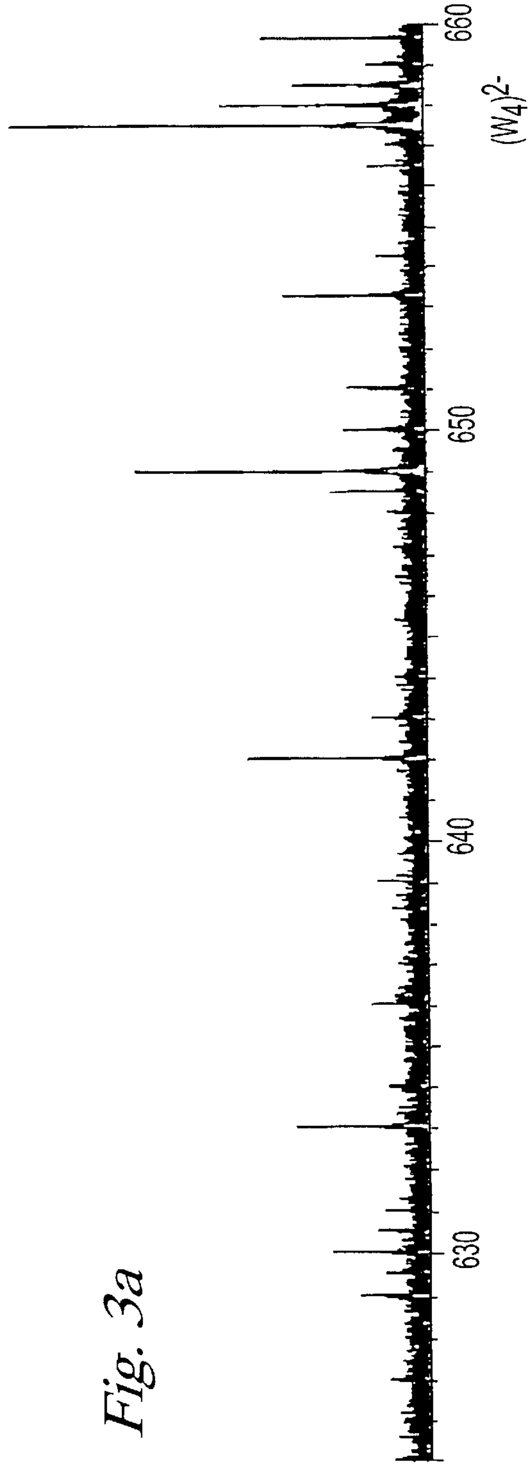
FIGS. 3*a* and 3*b* are expanded views of the mass spectra from FIGS. 2*b* and 2*c*, respectively, showing the region from 625 to 660.
Figure 3B:
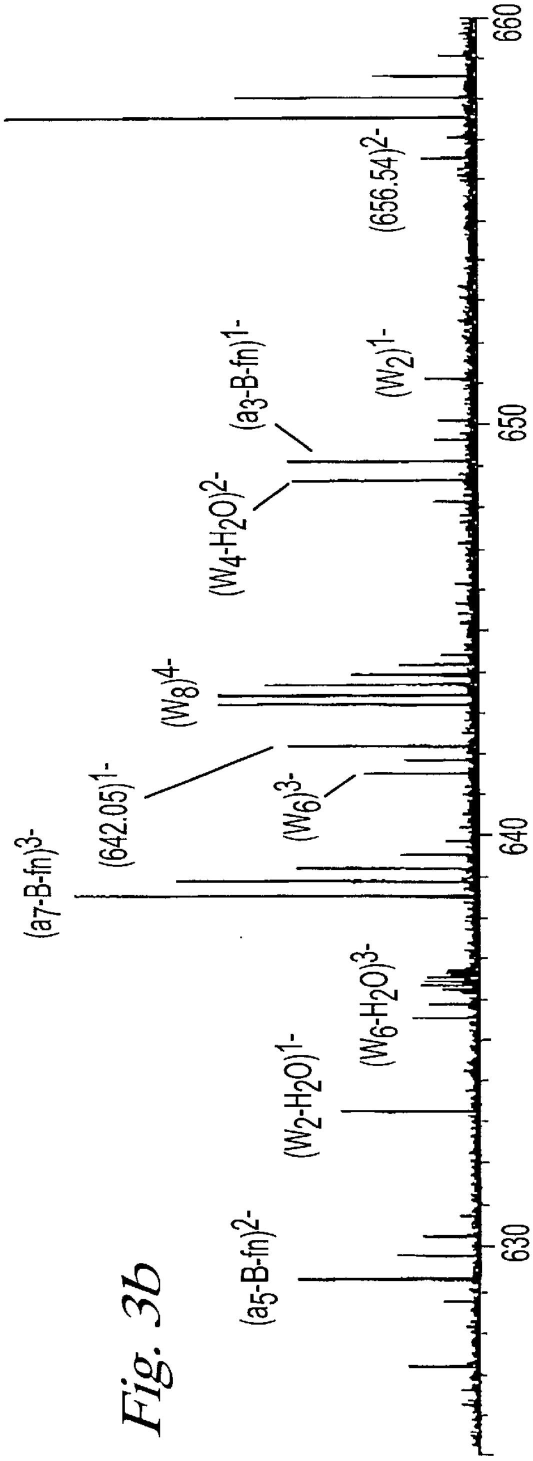

FIG. 2*a* contains a typical ESI-FTICR spectrum of a 20-mer phosphorothioate oligonucleotide obtained by externally accumulating ions for 500 ms prior to injection and detection in the FTICR cell. FIG. 2*b* contains an ESI-FTICR spectrum obtained from in-cell IRMPD effected by externally accumulating ions for 500 ms in the external ion reservoir, transferring them to the trapped ion cell, and then irradiating them for 100 ms. FIG. 2*c* contains an IRMPD ESI-FTICR spectrum obtained from externally accumulating ions for 500 ms concurrent with IR irradiation in the external reservoir. Following the accumulation/irradiation interval, the ions are transferred to the trapped ion cell where they are mass analyzed. While a significant degree of fragmentation is observed from the in-cell IRMPD as shown in FIG. 2*b*, the majority of the assignable fragment ions correspond to relatively low molecular weight singly charged fragments consistent with w and a-base ions and their respective decomposition products including neutral base loss and dehydration. From the collection of fragment ions detected, only 6 bases from the 5'end and 6 bases from the 3' of the analyte can be unambiguously assigned. Very few fragment ions are present at multiple charge states and there is insufficient fragmentation to determine the entire sequence of the oligonucleotide. As evidenced by FIGS. 3*a* and 3*b*, the spectrum in FIG. 2*c* is rich in fragment ions corresponding to a wide range of charge states (1- to 5-) and molecular weights and provides greater information than in-cell IRMPD. Full coverage of the oligonucleotide sequence is observed with most w and a-base ions observed at multiple charge states. In addition to an improvement in fragment ion abundance and sequence coverage, the spectrum acquired with the external IRMPD scheme exhibits improved resolving power and signal-to-noise relative to the spectrum acquired utilizing in-cell IRMPD.

Table 1 compares the fragment ions observed for the 20-mer phosphorothioate oligonucleotide employing three different dissociation techniques, nozzle-skimmer dissociation, in-cell IRMPD, and external IRMPD, all acquired under otherwise similar conditions. Note that while both nozzle-skimmer dissociation (FIG. 2*a*) and in-cell IRMPD (FIG. 2*b*) result in 5' fragments extending only to the $a_7$-base ion, the external IRMPD scheme provides multiple charge states of fragment ions extending to the $a_{,13}$-base. Similarly, from the 3' end of the molecule, nozzle-skimmer and in-cell IRMPD provide fragment ions out to the $w_9$ and $W_7$ species, respectively, while the external IRMPD scheme provides w ions as large as the $w_{13}$ ion. In general the external IRMPD scheme provides more charge states of each fragment than the other methods. For example, while nozzle-skimmer dissociation produces the 2-charge state for the $w_7$, $w_8$, and $w_9$ species, the external IRMPD scheme produces the 2-, 3-, and 4-charge state for each of these species providing further confirmation of these sequence specific ions.

Table 1: Fragment ions observed for a 20-mer phosphorothioate oligonucleotide using three dissociation techniques: nozzle-skimmer (DNS), IRMPD in the trapped ion cell of a FTICR mass spectrometer (in-cell IRMPD), and IRMPD effected in the external ion reservoir with subsequent detection by FTICR (Hexapole IRMPD).

The numbers in each column correspond to the charge state(s) of the fragments observed. All ions are negatively charged.

| Fragment | DNS | in-cell IRMPD | Hexapole IRMPD |
|---|---|---|---|
| a2-base | 1 | 1 | 1 |
| a3-base | 1 | 1 | 1 |
| a4-base | 1 | 1,2 | 1,2 |
| a5-base | 1 | 1,2 | 1,2 |
| a6-base | 1 | 2 | |
| a7-base | 1 | 2 | 2,3 |
| a8-base | | | 2,3 |
| a9-base | | | |
| a10-base | | | 2,3 |
| a11-base | | | 3,4 |
| a12-base | | | 4 |
| al3-base | | | 3,4 |
| w2 | | 1 | 1 |
| w3 | 1 | 1,2 | 1,2 |
| w4 | 1 | 2 | 1,2 |
| w5 | 1 | 2 | 2,3 |
| w6 | | | 3 |
| w7 | 2 | 2,3 | 2,3,4 |
| w8 | 2 | | 2,3,4 |
| w9 | 2 | | 2,3,4 |
| wl0 | | | 3,4 |
| wll | | | |
| w12 | | | |
| w13 | | | 3,4 |

Example 3

Comparison of Mass Spectrometry Methods With Ubiquitin

Figure 4:
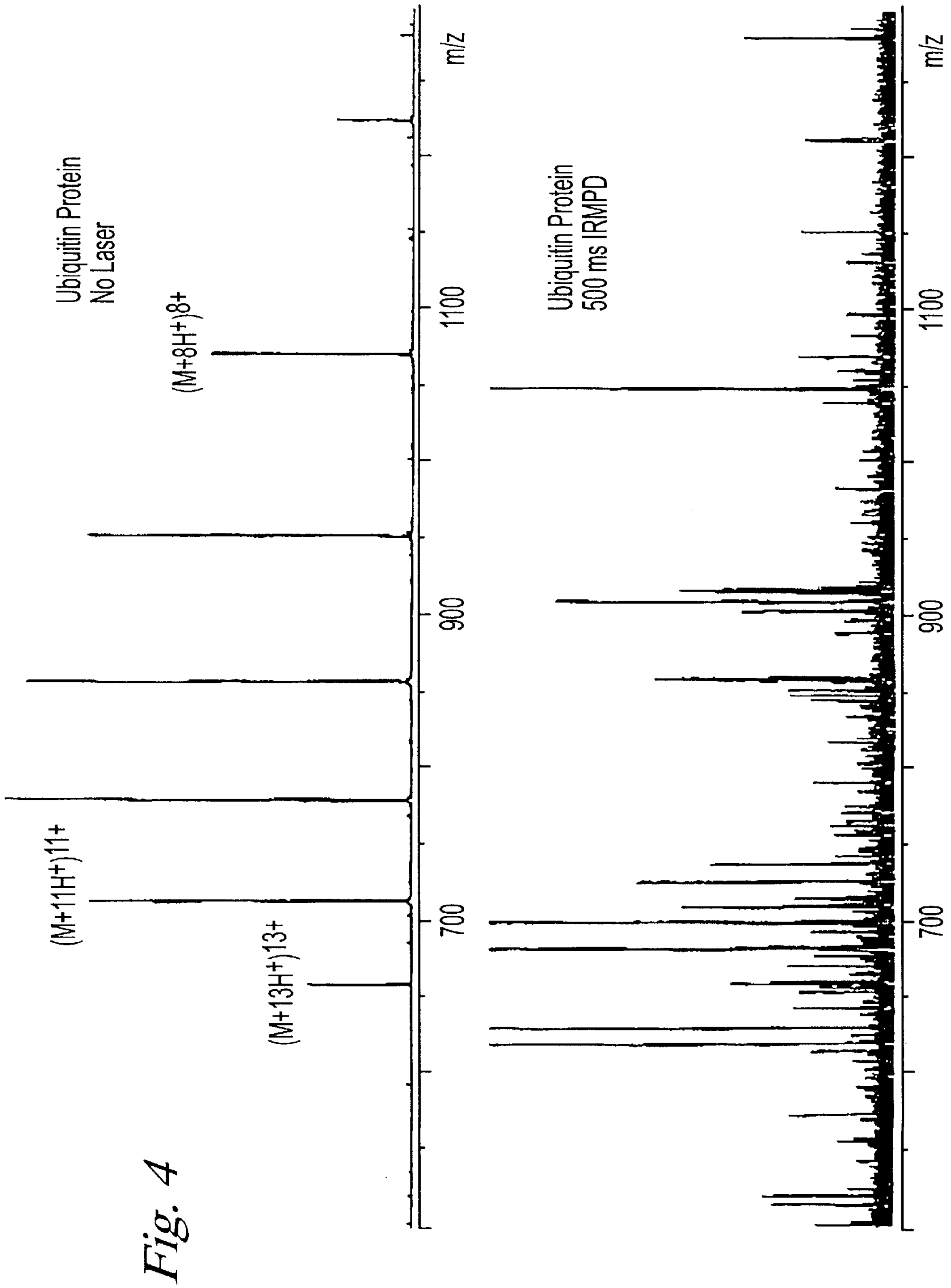
FIG. 4 is a series of mass spectra for ubiquitin. The top spectrum represents non-IRMPD mass spectrometry, while the bottom spectrum represents IRMPD in which the dissociation was performed in the external ion reservoir concurrent with ion accumulation.

ESI-FTICR spectra of ubiquitin acquired from a 10 mM 50:50 $H_2O$:MeOH solution with 1% HOAc. The spectrum in a) was acquired following a 500 ms ion accumulation interval in the external ion reservoir, the spectrum in b) was acquired employing a 500 ms ion accumulation interval during which the $CO_2$ laser was traversing the ion reservoir. The spectra obtained are shown in FIG. 4.

What is claimed is:

1. A method of inducing dissociation of molecular ions prior to analysis in a mass analyzer of a mass spectrometer, comprising the steps of:

(a) generating said molecular ions by ionization;

(b) accumulating said ions in an ion reservoir that is external to the mass analyzer; and (c) during the accumulation of said ions in said ion reservoir, exposing said ions in said reservoir to coherent radiation to dissociate said ions prior to mass analysis in a mass analyzer of a mass spectrometer;

wherein said exposing results in the production of multiple charge states of fragment ions.

2. The method of claim 1 wherein said accumulating of ions occurs in a m/z range of from about 50 to about 100,000.

3. The method of claim 1 wherein said ion reservoir is a rf trap or Penning trap.

4. The method of claim 3 wherein said rf trap is a rf-multi-pole ion reservoir.

5. The method of claim 4 wherein said rf-multi-pole ion reservoir is a quadrupole, hexapole or octapole ion reservoir.

6. The method of claim 1 wherein said ion reservoir is evacuated to $10^{-3}$ to $10^{-6}$ torr.

7. The method of claim 1 wherein said coherent radiation is emitted from a laser.

8. The method of claim 7 wherein said laser is an infrared laser.

9. The method of claim 1 wherein said mass analyzer is a trapped ion cell of a Fourier transform ion cyclotron mass spectrometer, a time-of-flight mass spectrometer, a quadropole ion trap mass spectrometer, a quadrupole mass analyzer, or a magnetic/electric sector mass spectrometer.

10. A method of inducing dissociation of molecular ions prior to analysis in a mass analyzer of a mass spectrometer, comprising the steps of:

(a) generating said molecular ions by ionization;

(b) accumulating said ions in an ion reservoir that is external to the mass analyzer; and (c) exposing said ions in said reservoir to coherent radiation for a time sufficient for dissociation of said ions into fragments having multiple charge states prior to mass analysis in a mass analyzer of a mass spectrometer.

11. The method of claim 10 wherein said accumulating of said ions occurs in a m/z range of from about 50 to about 100,000.

12. The method of claim 10 wherein said ion reservoir is an rf trap or a Penning trap.

13. The method of claim 12 wherein said rf trap is an rf-multipole ion reservoir.

14. The method of claim 13 wherein said rf-multipole ion reservoir is a quadrupole, hexapole, or octapole ion reservoir.

15. The method of claim 10 wherein said ion reservoir is evacuated to 10-3 to 10-; torr.

16. The method of claim 10 wherein said coherent radiation is emitted from a laser.

17. The method of claim 16 wherein said laser is an infrared laser.

18. The method of claim 10 wherein said mass analyzer is a trapped ion cell of a Fourier transform ion cyclotron mass spectrometer, a time-of-flight mass spectrometer, a quadropole ion trap mass spectrometer, a quadrupole mass analyzer, or a magnetic/electric sector mass spectrometer.

* * * * *